(12) United States Patent  
Chacon et al.

(10) Patent No.: US 8,410,942 B2  
(45) Date of Patent: Apr. 2, 2013

(54) SYSTEMS AND METHODS TO ADJUST AN ADJUSTABLE BED

(75) Inventors: Ryan Chacon, Carthage, MO (US); Niels S. Mossbeck, Carthage, MO (US); Thomas W. Wells, Joplin, MO (US)

(73) Assignee: L&P Property Management Company, South Gate, CA (US)

( * ) Notice: Subject to any disclaimer, the term of this patent is extended or adjusted under 35 U.S.C. 154(b) by 500 days.

(21) Appl. No.: 12/787,091

(22) Filed: May 25, 2010

(65) Prior Publication Data

US 2010/0302044 A1 Dec. 2, 2010

Related U.S. Application Data

(60) Provisional application No. 61/182,443, filed on May 29, 2009.

(51) Int. Cl.  
    *G08B 23/00* (2006.01)
(52) U.S. Cl. .................. 340/575; 340/573.1; 340/573.7
(58) Field of Classification Search .................. None  
    See application file for complete search history.

(56) References Cited

U.S. PATENT DOCUMENTS

| | | | |
|---|---|---|---|
| 3,089,130 A | | 5/1963 | Wilson |
| 3,998,209 A | * | 12/1976 | Macvaugh .................. 128/848 |
| 4,220,142 A | | 9/1980 | Rosen et al. |
| 4,848,360 A | * | 7/1989 | Palsgard et al. .............. 600/586 |
| 5,042,097 A | * | 8/1991 | Fuchs ................................. 5/607 |
| 5,458,105 A | * | 10/1995 | Taylor et al. .................. 128/848 |
| 5,684,460 A | | 11/1997 | Scanlon |
| 6,371,120 B1 | * | 4/2002 | Chiu et al. ..................... 128/848 |
| 6,468,234 B1 | * | 10/2002 | Van der Loos et al. ........ 600/595 |
| 7,007,327 B2 | | 3/2006 | Ogawa et al. |
| 7,093,312 B2 | * | 8/2006 | Mossbeck ......................... 5/613 |
| 7,513,003 B2 | * | 4/2009 | Mossbeck ......................... 5/731 |
| 7,522,062 B2 | * | 4/2009 | Mossbeck ..................... 340/575 |
| 7,716,988 B2 | * | 5/2010 | Ariav et al. ..................... 73/597 |
| 2004/0234080 A1 | | 11/2004 | Hernandez et al. |
| 2006/0026763 A1 | * | 2/2006 | Mossbeck ......................... 5/618 |
| 2006/0162074 A1 | * | 7/2006 | Bader ................................. 5/421 |
| 2008/0052837 A1 | | 3/2008 | Blumberg |
| 2008/0155750 A1 | * | 7/2008 | Mossbeck ......................... 5/618 |
| 2008/0264426 A1 | * | 10/2008 | Walker ............................ 128/848 |
| 2008/0282471 A1 | | 11/2008 | Chambers et al. |
| 2009/0177327 A1 | * | 7/2009 | Turner et al. .................. 700/275 |
| 2009/0250070 A1 | | 10/2009 | Pfeifer |
| 2010/0283618 A1 | * | 11/2010 | Wolfe et al. .................... 340/575 |

* cited by examiner

*Primary Examiner* — Travis Hunnings  
(74) *Attorney, Agent, or Firm* — Wood, Herron & Evans, LLP (57) ABSTRACT

A system and method provide for reducing the snoring of a person sleeping on an adjustable bed. The system comprises a device configured with at least a microphone and a speaker, the device configured to monitor for a noise consistent with snoring. The system further comprises a control unit communicably coupled to the device and configured to actuate at least one motor of the adjustable bed to adjust at least a portion of the adjustable bed, wherein the control unit is further configured to actuate the at least one motor in response to the device detecting a noise consistent with snoring.

29 Claims, 7 Drawing Sheets

SYSTEMS AND METHODS TO ADJUST AN ADJUSTABLE BED

CROSS REFERENCE TO RELATED APPLICATIONS

This application claims the benefit of provisional Patent Application No. 61/182,443 filed May 29, 2009, which is fully incorporated herein.

FIELD OF THE INVENTION

The present invention relates to bedding products, and more particularly to controlling a bed in such a manner as to effect the snoring of a person sleeping thereupon.

BACKGROUND OF THE INVENTION

Snoring may disturb persons sleeping in the same room or on the same bed as the person snoring. From time to time snoring can become so loud that it may even awaken the snoring person or others in the same room or bed. Some may deal with a snorer by waking him/her up to cause the snoring to stop, but this causes the snorer's sleep to be interrupted. Furthermore, after going back to sleep, snoring may start again, often shortly afterwards.

Snoring may occur when soft tissue in the back of a person's mouth relaxes during sleep, especially when a person sleeps on his or her back. The relaxation of the tissue may partially block the airway, which causes the body of the person to react by breathing harder, which in turn causes vibration of the tissue that results in a snoring sound. In some cases it has been determined that the snoring sounds do not occur if and as long as the person concerned sleeps in a particular position, such as lying on his or her side. Fewer people tend to snore when lying on their side, as the soft tissue may not obstruct the airway in the same manner as when the person is lying on his or her back.

Various ways have been developed to prevent snoring. Some conventional devices seeking to address this problem have variously forced a person to sleep on their side, which may not be conductive to restful sleep for some persons. Other conventional devices have disposed a vibrator in the head of the bed to actuate upon snoring, but often the actuation of the vibrator interrupts the sleep of the person. Still other conventional devices have used a speaker to subconsciously cause a change of behavior in a snoring person. Furthermore, still other conventional devices have used a vibrator to influence a person to change their sleeping position.

Consequently, there is a need for a system and associated method suitable to stop a person's snoring by changing his or her sleeping position without substantially disturbing his/her sleep, and, in the event that does not work, to selectively awaken the person.

SUMMARY OF THE INVENTION

These and other problems of conventional devices are addressed by embodiments of the invention, which provide a system and method to reduce snoring of a person sleeping on an adjustable bed. In some embodiments, the system comprises a device configured with at least a microphone and a speaker, the device configured to monitor for a noise consistent with snoring. The system further comprises a control unit communicably coupled to the device and configured to actuate at least one motor of the adjustable bed to adjust at least a portion of the adjustable bed, wherein the control unit is further configured to actuate the at least one motor in response to the device detecting a noise consistent with snoring.

These and other advantages will be apparent in light of the following figures and detailed description.

BRIEF DESCRIPTION OF THE DRAWINGS

The accompanying drawings, which are incorporated in and constitute a part of this specification, illustrate embodiments of the invention and, together with a general description of the invention given above and the detailed description of the embodiments given below, serve to explain the principles of the invention.

It should be understood that the appended drawings are not necessarily to scale, presenting a somewhat simplified representation of various features illustrative of the basic principles of embodiments of the invention. The specific design features of embodiments of the invention as disclosed herein, including, for example, specific dimensions, orientations, locations, and shapes of various illustrated components, as well as specific sequences of operations (e.g., including concurrent and/or sequential operations), will be determined in part by the particular intended application and use environment. Certain features of the illustrated embodiments may have been enlarged or distorted relative to others to facilitate visualization and clear understanding.

DETAILED DESCRIPTION

Hardware and Software Environment

Figure 1:
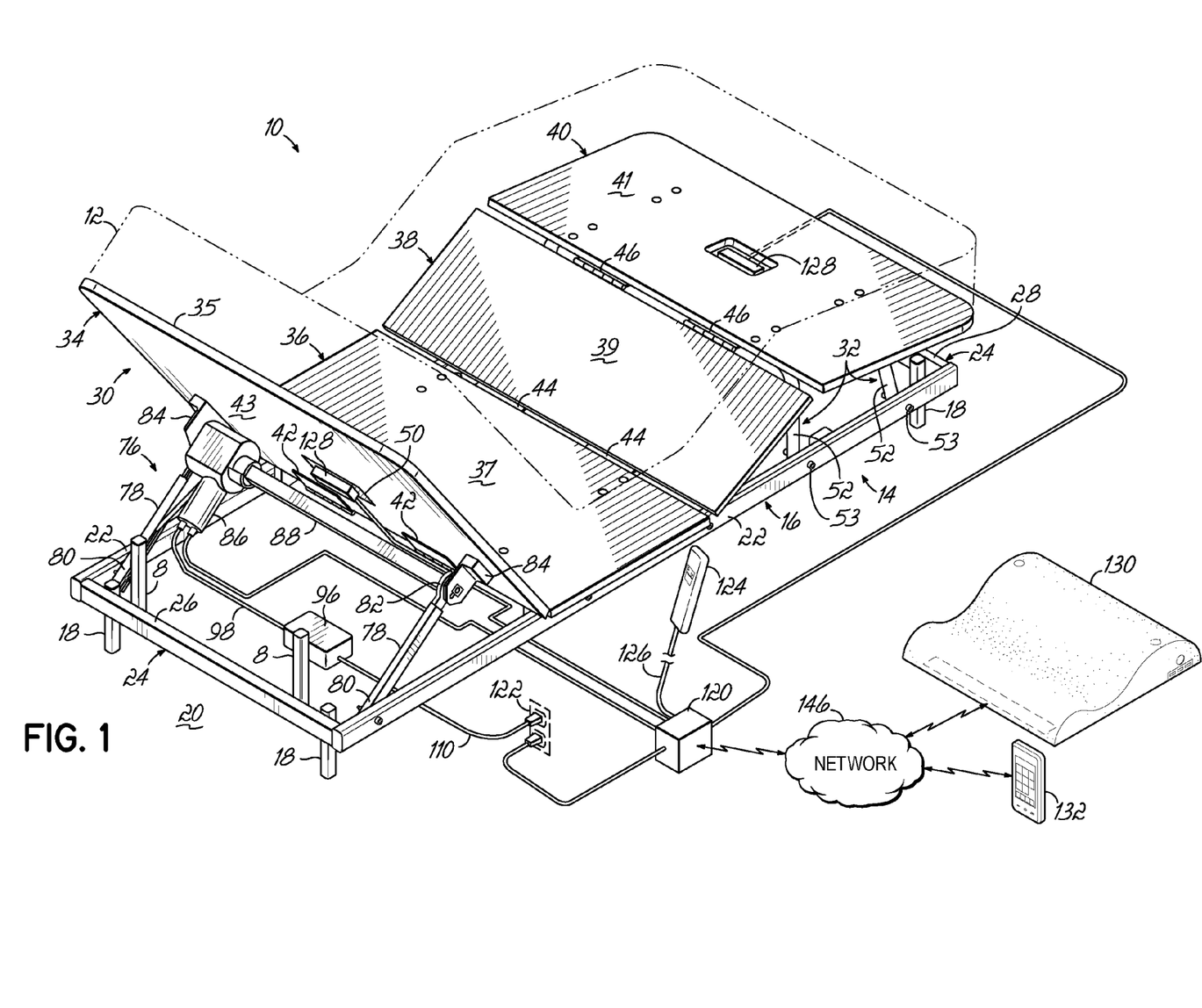
FIG. 1 is perspective view of an adjustable bed made in accordance with the principles of this invention in a fully inclined position supporting a mattress shown in phantom consistent with embodiments of the invention.
Figure 2:
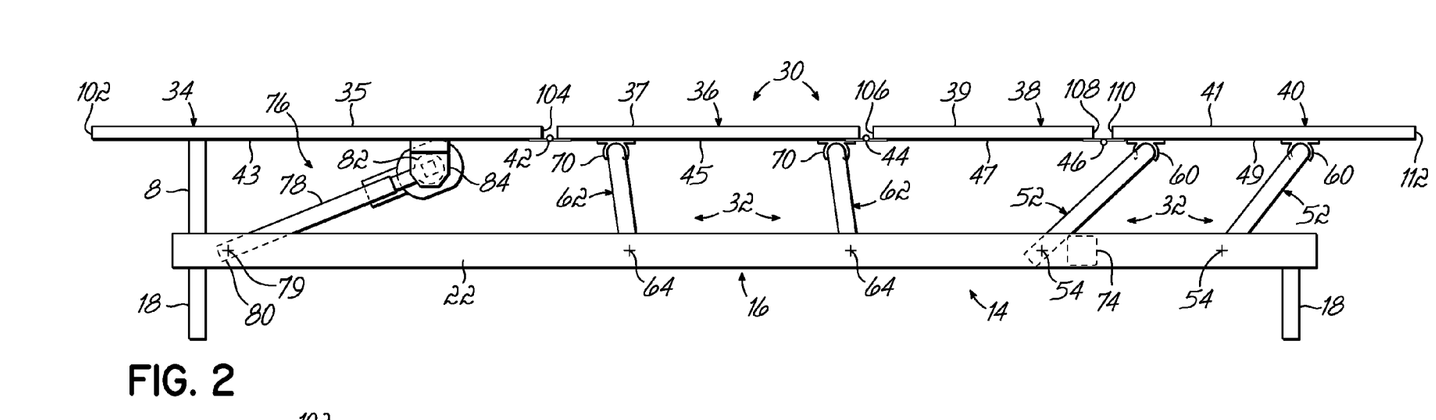
FIG. 2 is a side elevational view of the adjustable bed of FIG. 1 without the mattress and in a fully horizontal position.

Referring to the drawings, particularly to FIGS. 1-2, an exemplary bedding product in the form of an adjustable bed 10 includes a mattress 12 that can be of any conventional type such as an air mattress, a coil spring mattress, a mattress with at least one fluid reservoir (e.g., water or gas) or any other type of mattress. Similarly, the adjustable bed 10 may be any conventional adjustable bed, such as that described in U.S. Pat. No. 7,093,312, the disclosure of which is herein incorporated by reference in its entirety.

With reference to FIG. 2, the adjustable bed 10 is movable between a fully horizontal position and a fully inclined position (FIG. 1). An operator or user may sleep with the adjustable bed 10 generally in its fully horizontal position, in the fully inclined position, or in any position therebetween.

The adjustable bed 10 may comprise a base 14 including a generally rectangular stationary frame 16 and four legs 18 supporting the frame 16 a fixed distance about a floor or supporting surface 20. The stationary frame 16 comprises a pair of opposed side rails 22 and a pair of opposed end rails 24 extending between the side rails 22 at the ends thereof. The end rails 24 include a head rail 26 and a foot rail 28. The legs 18 may be secured to the end rails 24 or may alternatively be secured to the side rails 22.

Figure 3:
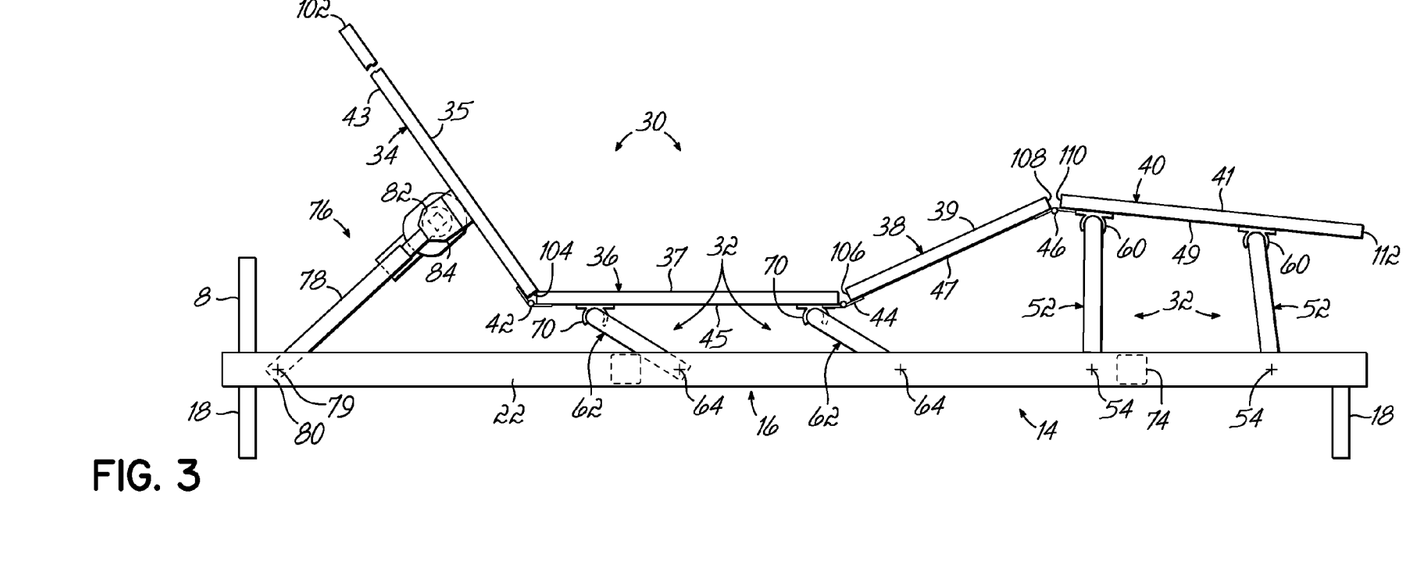
FIG. 3 is a side elevational view of the adjustable bed of FIG. 1 without the mattress and in a fully inclined position.

With reference to FIGS. 2-3, an articulated deck 30 is spaced above the stationary frame 16 with a plurality of connectors 32. The articulated deck 30 comprises a head deck board 34, a seat deck board 36, a leg deck board 38 and a foot deck board 40. The deck boards may be of equal width but any two deck boards may alternatively be of different widths. Deck boards 34, 36, 38 and 40 have upper surfaces 35, 37, 39 and 41, respectively, and lower surfaces 43, 45, 47 and 49, respectively.

Figure 4:
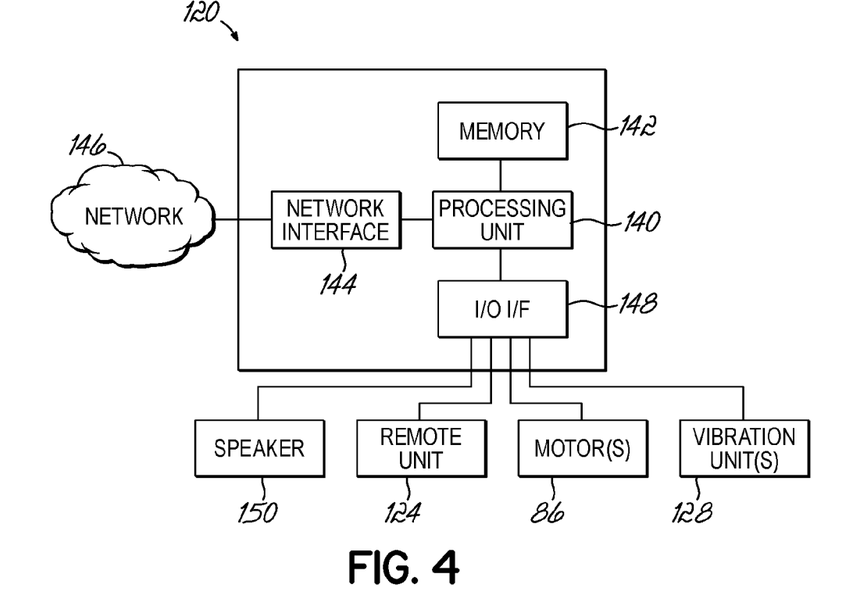
FIG. 4 is a diagrammatic illustration of at least a portion of the control unit of FIG. 1.

The head deck board 34 is hingedly secured to the seat deck board 36 with hinges 42, in turn secured to the lower surfaces 43, 45 of the head and seat deck boards 34, 36, respectively. Similarly, seat deck board 36 is hingedly secured to leg deck board 38 with hinges 44, in turn secured to the lower surfaces 45, 47 of the seat and leg deck boards 36, 38, respectively. Leg deck board 38 is hingedly secured to foot deck board 40 with hinges 46, in turn secured to the lower surfaces 47, 49 of the leg and foot deck boards 38, 40, respectively. Although two hinges 42 are shown (FIGS. 1-4) securing the head deck board 34 to the seat deck board 36, any number of hinges may alternatively be used including one continuous hinge. The same applies to hinges 44 and 46 connecting the other deck boards. The deck boards 34, 36, 38 and 40 may be made of plywood, or may alternatively comprise plastic, oriented strand board or any other suitable material. As illustrated in FIGS. 1 and 4, the head deck board 34 may include a rectangular aperture 50 or an aperture of any suitable shape therein which may be used as a handle.

With continued reference to FIGS. 2-3, the adjustable bed 10 further comprises connectors 32 in the form of inverted U-shaped foot tubes 52. The adjustable bed 10 has two foot tubes 52 pivotally secured to the side rails 22 of the stationary frame 16 with fasteners 53 so that each pivots about a horizontal pivot axis 54. Each foot tube 52 has a center portion 56 and a pair of leg portions 58 extending downwardly from opposed ends of the center portion 56. The center portion 56 of each of the foot tubes 52 is secured to the foot deck board 40 with clips 60. Clips 60 are each secured to the lower surface 49 of the foot deck board 40. Although each foot tube 52 is illustrated being secured to two clips 60, any other methods and/or components for securing the foot tubes 52 to the foot deck board 40 may alternatively be used.

Two seat tubes or connectors 62 are pivotally secured to the side rails 22 of the stationary frame 16 with fasteners 63 so that each pivots about a horizontal pivot axis 64. Each seat tube 62 has a center portion 66 and a pair of leg portions 68 extending downwardly from opposed ends of the center portion 66. The center portion 66 of each of the foot tubes 62 is secured to the seat deck board 36 with clips 70. Clips 70 are secured to the lower surface 45 of the seat deck board 36. Although each seat tube 62 is illustrated being secured to two clips 70, any other methods and/or components for securing the seat tubes 62 to the seat deck board 36 may alternatively be used.

With reference to FIGS. 2-3, two stops 72 are each secured to the inside surfaces of the side rails 22 of the frame 16 to prevent the seat tubes 62 from moving too far forwardly i.e. towards the head end of the bed. Similarly, two stops 74 are each secured to the inside surfaces of the side rails 22 of the frame 16 to prevent the foot tubes 52 from moving too far rearward i.e. towards the foot end of the bed. The articulated deck 30 may be moved by a motorized drive assembly 76 between a fully horizontal position (FIG. 2) in which the deck boards 34, 36, 38 and 40 are generally co-planar in a horizontal position or orientation and a fully inclined position (FIG. 3). In the fully inclined position, the head deck board 34 is inclined, the seat deck board 36 is substantially horizontal, the leg deck board 36 inclined and the foot deck board 40 slightly inclined. When the articulated deck 30 is in its fully horizontal position (FIG. 2), two braces 8, each secured to the head rail 26 of the frame 18 and extending upwardly therefrom, support the head deck board 34 of the articulated deck 30.

The motorized drive assembly 76 may comprise two lever arms 78 pivotally secured at their respective lower ends 80 to the side rails 22 of the frame 16 such that each of the lever arms 78 pivots about a horizontal pivot axis 79. The lever arms 78 may have a fixed length. The upper ends 82 of the lever arms 78 are secured to brackets 84 which are, in turn, secured to the lower surface 43 of the head deck board 34. An electric motor 86 is secured to one of the lever arms 78. Alternatively, the electric motor 86 may be secured to the head deck board 34 or to any other suitable location or surface. The electric motor 86 maybe one of any suitable type, such as one manufactured by German manufacturer Hettich-Franke GmbH under the model designation Mosys Classic 1.61.03.

The output of the electric motor 86 drives or rotates a drive tube 88 that extends between the upper ends 82 of the lever arms 78. The electric motor 86 may be powered by a power supply 96 and may be controlled via a control unit 120. The power supply 96 and control unit 120 may be electrically powered, via respective connections, to a power source such as one in the form of a wall outlet 122. The control unit 120, in turn, may be controlled via a remote unit 124 communicably coupled to the control unit 120 as at 126.

In addition to controlling the electric motor 86, the control unit 120 may be configured to control at least one vibration unit 128. Each vibration unit 128 may be mechanically coupled to at least a portion of the adjustable bed 10 (such as a portion of the base 14 and/or frame 30) and/or the mattress 12 to allow a person (not shown) lying on the mattress 12 to experience a vibratory sensation. Although not shown, it will be appreciated that each vibration unit 128 may be powered by the power supply 96.

With reference to FIGS. 2-3, in operation, starting from the fully horizontal position of the adjustable bed 10 shown in FIG. 2 in which the articulated deck 30 is generally horizontal, the control unit 120 may be configured to actuate the motor 86 of the adjustable bed 10 in response to a determination that a person on the adjustable bed 10 is making a sound corresponding to snoring. Activation of the motor 86 rotates the drive tube 88 which causes the lever arms 78 of the drive assembly 76 to rotate or pivot about horizontal axis 79 at the lower ends 80 of the lever arms 78, i.e., where the lever arms 78 are pivotally secured to the side rails 22 of the frame 18. Thus, the head deck board 34 moves from its fully horizontal position (FIG. 2) to a second position (not shown) between the first horizontal position and the fully inclined position (FIG. 3) in which the head edge 102 of the head deck board 34 is above the rear edge 104 of the head deck board 34. The transition from the fully horizontal position to the second position may induce the snoring person to change sleeping positions, thereby causing the snoring to stop.

The control unit 120 may be configured to cause actuation of the electric motor 86 in one direction so as to cause the change in position described above from the fully horizontal position (FIG. 2) to a position between the fully horizontal position (FIG. 2) and the fully inclined position (FIG. 3). The control unit 120 may be further configured such that it will first detect the position of the head deck board 34 such that, if for example the head deck board 34 is in the second position, it will actuate the motor 86 to cause movement of the head deck board 34 from the second position to the fully horizontal position (FIG. 2) or to the fully inclined position (FIG. 3). Similarly, the control unit 120 may be configured such that it will first detect the position of the head deck board 34 and cause it to move from such position to any other position between the fully horizontal position (FIG. 2) and the fully inclined position (FIG. 3).

With continued reference to FIGS. 2-3, the control unit 120 may be also configured such that it causes the head deck board 34 to return from any starting position between the fully horizontal position (FIG. 2) and the fully inclined position (FIG. 3) back to the fully horizontal position (FIG. 2).

Movement of the head deck board 34 between the fully horizontal position (FIG. 2) and the fully inclined position (FIG. 3) may be also achieved via manual actuation of the remote unit 124. Remote unit 124 may be further configured such that it can cause movement of the head deck board 34 between any starting position and any desired ending position between and including the fully horizontal position (FIG. 2) and the fully inclined position (FIG. 3). Moreover, remote unit 124 may be configured such that it can control the vibratory characteristics of at least one vibration unit 128. A user of the adjustable bed 10 may, therefore, be able, for example, to move the bed 10 from any starting position to the fully inclined position (FIG. 3) as well as create the vibratory sensation. In such exemplary motion, as the head deck board 34 inclines, the person using the bed 10 may lean forward causing the rear edge 104 of the head deck board 34 to move towards the head end of the bed, causing or pulling the seat deck board 36 horizontally towards the head end of the bed. The seat deck board 36 also lowers due to the connectors 32 and more particularly, the seat tubes 62 pivoting about horizontal pivot axes 64 in a counterclockwise direction as shown in FIGS. 2-3.

With continued reference to FIGS. 2-3, as the seat deck board 36 moves downwardly and towards the head end of the bed, the leg deck board 38 moves or is pulled from its fully horizontal position (FIG. 2) to its fully inclined position (FIG. 3). In this fully inclined position, the front edge 106 of the leg deck board 38 is lower than the rear edge 108 of the leg deck board 38. This movement of the leg deck board 38 causes or pulls the foot deck board 40 towards the head end of the bed as the connectors 32 and in particular the foot tubes 52 are pivoted about horizontal pivot axes 54 in a counterclockwise direction. In its fully inclined position (FIG. 3), the front edge 110 of the foot deck board 40 is higher than the rear edge 112 of the foot deck board 40.

The adjustable bed 10 may be also moved from its fully inclined position (FIG. 3), in which the front edge 102 of the head deck board 34 is above the rear edge 104 of the head deck board 34, back to its fully horizontal position (FIG. 2) via use of the motorized drive assembly 76 along with the person using the bed 10 shifting his or her weight backwardly.

The control unit 120 may communicably coupled with an interactive pillow 130 and/or a portable electronic device 132. In some embodiments, the control unit 120 is configured to communicate with the interactive pillow 130 and/or the portable electronic device 132 wirelessly. Specifically, the control unit 120 may be configured to communicate with the interactive pillow 130 and/or the portable electronic device 132 through radio frequency communications, such as, for example, using a wireless local area network (e.g., a "WLAN," such as Wi-Fi®) and/or a low power wireless protocol (e.g., Bluetooth®).

In some embodiments, the interactive pillow 130 is configured with a pillow portion (e.g., such as a molded latex, foam material and/or other stuffing material) and a hardware portion. The interactive pillow 130 is configured to sense human activity, such as snoring and/or motion, and communicate with the control unit 130 to indicate that information as well as adjust and/or awaken the person. Similarly, the portable electronic device 132 may be an electronic device configured to sense snoring and/or motion, and communicate with the control unit 130 to indicate that information as well as adjust and/or awaken the person. The portable electronic device 132, however, may be a communication device, such as a cell phone and/or smart phone, or an entertainment device, such as a portable gaming system, music player, etc. In specific embodiments, the portable electronic device 132 is an iPhone® and/or iTouch® as distributed by Apple Computer, Inc., of Cupertino, Calif.

In some embodiments, the control unit 120 is a computing apparatus configured to control the motor 86, the at least one vibration unit 128 and/or another component to adjust and/or awaken a person on the bed 10 who is or has been snoring or moving thereupon. FIG. 4 is a diagrammatic illustration of at least a portion of the control unit 120 consistent with embodiments of the invention. The control unit 120, in specific embodiments, may be a computer, computer system, computing device, server, disk array, or programmable device such as a multi-user computer, a single-user computer, a handheld device, a networked device (including a computer in a cluster configuration), a mobile phone, a video game console (or other gaming system), etc. Specifically, the control unit 120 includes at least one processing unit 140 coupled to a memory 142 and may be configured to communicate through at least one network interface 144 (hereinafter, "network I/F" 144) with at least one network 146.

The control unit 120 may be coupled to the motor 86, remote unit 124 and/or the at least one vibration unit 128 through an input/output device interface 148 (illustrated as, and hereinafter, "I/O I/F" 148). Moreover, the control unit 120 may also include peripheral devices connected through the I/O I/F 148. In particular, the control unit 120 may receive data from a person through the remote unit 124 and/or output audio to the person through at least one speaker 150.

Figure 5A:
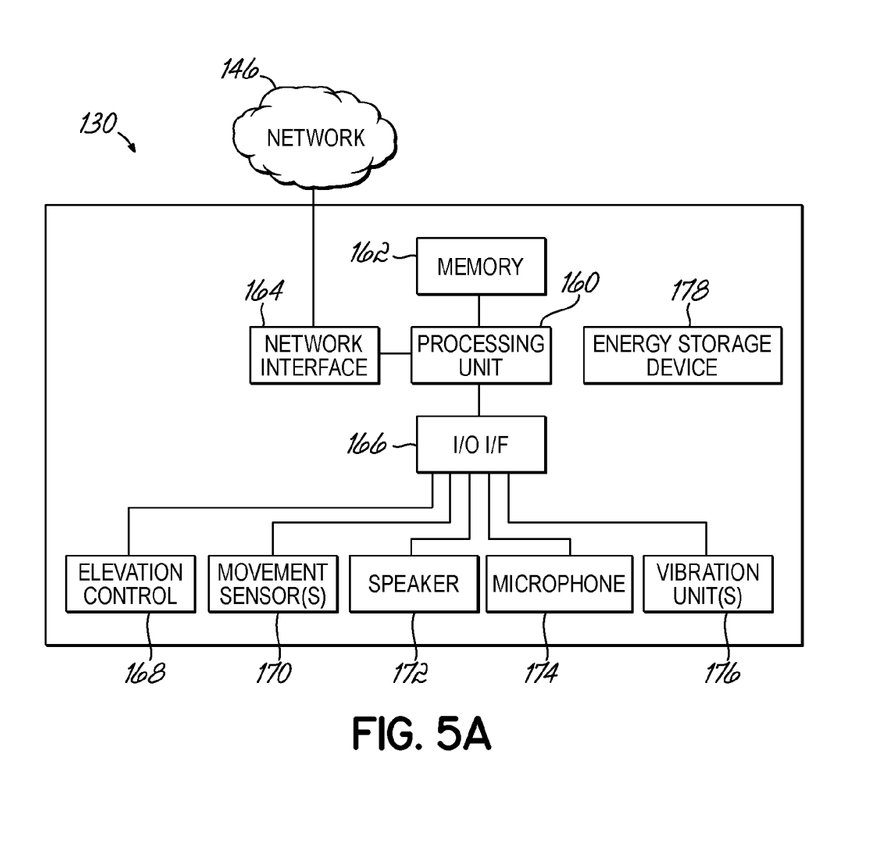
FIG. 5A is a diagrammatic illustration of at least a portion of the interactive pillow of FIG. 1 further illustrating the hardware portion of the interactive pillow.
Figure 5B:
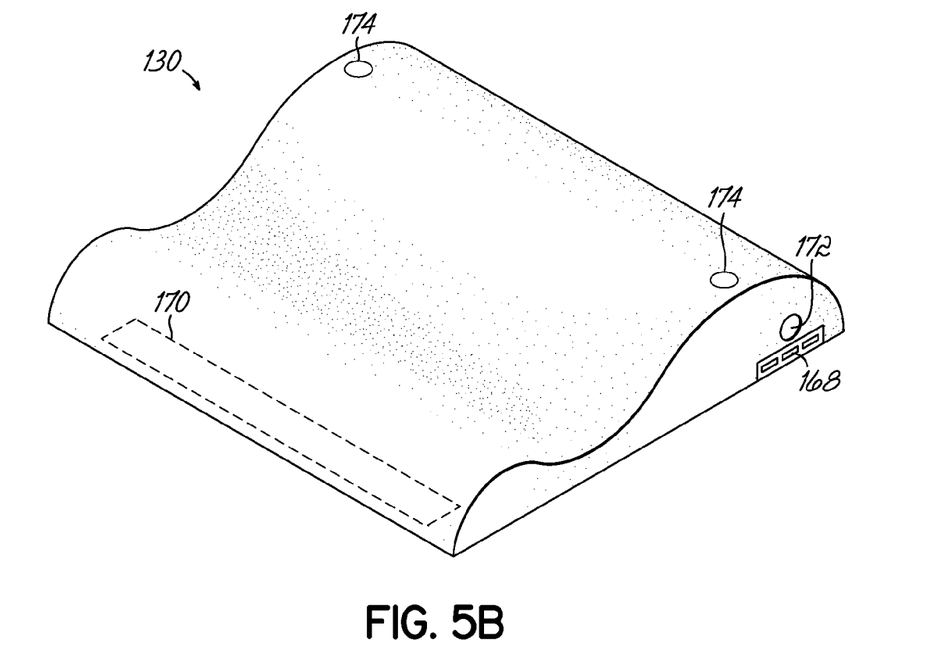
FIG. 5B is a perspective illustration of the interactive pillow of FIG. 1.

FIG. 5A is a diagrammatic illustration of at least a portion of the interactive pillow 130 consistent with embodiments of the invention while FIG. 5B is a perspective illustration of one embodiment of the interactive pillow 130 consistent with embodiments of the invention. Similarly to the control unit 120, the interactive pillow 130 includes at least one processing unit 160 coupled to a memory 162 and communicates through at least one network interface 164 (hereinafter, "network I/F" 164) with the at least one network 146. Moreover, the interactive pillow 130 may include an input/output device interface 166 (illustrated as, and hereinafter, "I/O I/F" 166) to interact with at least one peripheral device connected through the I/O I/F 166. With reference to FIG. 5A and FIG. 5B, the interactive pillow 130 may be configured to receive a request to raise and/or lower at least a portion of the adjustable bed 10 from at least one elevation control 168 as well as determine the presence of the person and/or movement thereof through at least one movement sensor 170. The at least one elevation control 168 may include buttons to request that at least a portion of the adjustable bed 10 be raised and/or lowered, while the at least one movement sensor 170 may include at least one micro switch configured to detect contact of the person with the interactive pillow 130. Alternatively, the at least one movement sensor 170 may include at least one gyroscope and/or accelerometer to detect the movement of the person.

Furthermore, the interactive pillow 130 may include a speaker 172 to output audio to the person, a microphone 174 to detect snoring and/or voiced utterances of the person, as well as a vibration unit 176 to produce a vibratory sensation, such as to awaken the person. Additionally, the interactive pillow 130 may include an energy storage device 178, such as at least one battery (e.g., rechargeable and/or disposable) and/or at least one capacitor (e.g., including at least one super-capacitor). Moreover, and although not illustrated in FIG. 5A or FIG. 5B, the interactive pillow 130 may include at least one light (not shown). Specifically, the light may be configured as a soft light similar to a night light and/or as an indication light, such as to indicate that the energy storage device 178 is running low.

Figure 6:
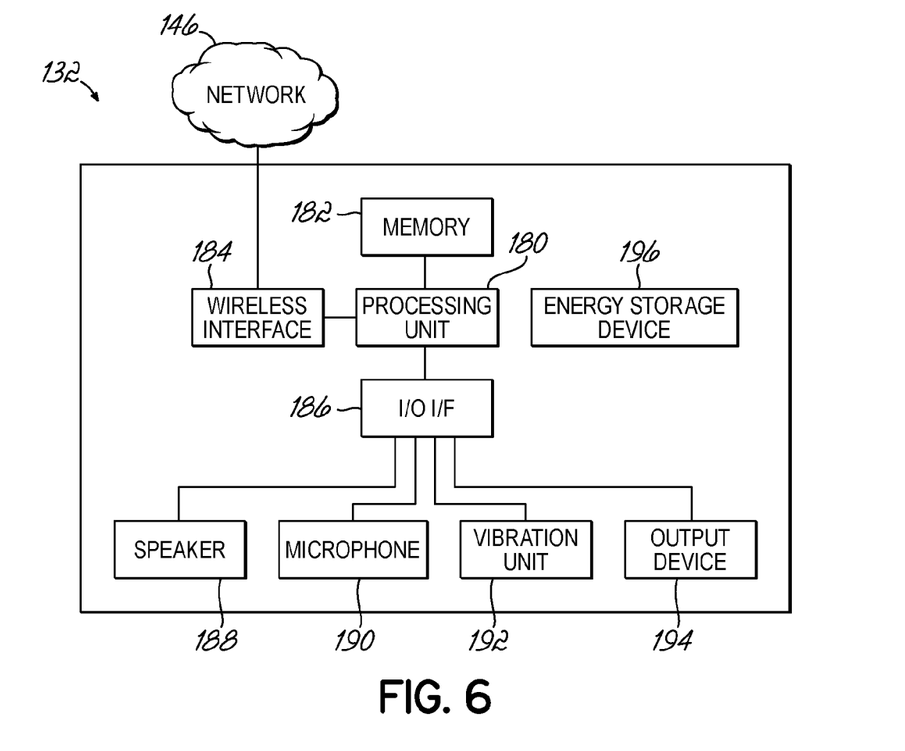
FIG. 6 is a diagrammatic illustration of at least a portion of the portable electronic device of FIG. 1.

FIG. 6 is a diagrammatic illustration of at least a portion of the portable electronic device 132 consistent with embodiments of the invention. Similarly to the control unit 120 and/or the interactive pillow 130, the portable electronic device 132 includes at least one processing unit 180 coupled to a memory 182 and may communicate through at least one network interface 184 (hereinafter, "network I/F" 184) with the at least one network 146. As illustrated in FIG. 6, the portable electronic device 132 may include an input/output device interface 186 (illustrated as, and hereinafter, "I/O I/F" 186) to interact with at least one peripheral device connected through the I/O I/F 186. Specifically, the portable electronic device 132 may be configured to output audio to the person through a speaker 188 as well as detect snoring and/or voiced utterances of the person through a microphone 190. Moreover, the portable electronic device 132 may include a vibration unit 192 to produce a vibratory sensation and/or an output device 194 (including, for example, a display, a touchscreen, a printer, and/or another output device) to output data. Specifically, the output device 194 may be a video display device. In specific embodiments, the output device 194 is a touchscreen display. Additionally, the portable electronic device 132 may include an energy storage device 196, such as at least one battery (e.g., rechargeable and/or disposable) and/or at least one capacitor (e.g., including at least one super-capacitor).

Although not illustrated, it will be appreciated that the remote unit 124 may include a speaker, a light and/or an output device. Moreover, the remote unit 124 may include a microphone, processing unit and/or memory. Furthermore, the remote unit 124 may include a wireless interface and communicate with the control unit 120 through the network 146.

Each processing unit 140, 160 and/or 180 is typically implemented in hardware using circuit logic disposed on one or more physical integrated circuit devices or chips. It will be appreciated that each processing unit 140, 160 and/or 180 may be a different type of processing unit consistent with embodiments of the invention. Each processing unit 140, 160 and/or 180 may be one or more microprocessors, microcontrollers, field programmable gate arrays, or ASICs, while respective memory 142, 162 and/or 182 may include random access memory (RAM), dynamic random access memory (DRAM), static random access memory (SRAM), flash memory, and/or another digital storage medium, and also typically implemented using circuit logic disposed on one or more physical integrated circuit devices, or chips. As such, memory 142, 162 and/or 182 may be considered to include memory storage physically located elsewhere in the respective control unit 120, interactive pillow 130 and/or portable electronic device 132, e.g., any cache memory in the at least one respective processing unit 140, 160 and/or 180, as well as any storage capacity used as a virtual memory, e.g., as stored on a mass storage device, a computer, or another controller coupled through at least one respective network I/F 144, 164 and/or 184 by way of the at least one network 146. It will be appreciated that the at least one network 146 may include at least one private communications network (e.g., such as an intranet) and/or at least one public communications network (e.g., such as the Internet). Moreover, it will be appreciated that the at least one network 146 may include at least one wired network (e.g., such as an Ethernet network) and/or at least one wireless network (e.g., such as a WLAN and/or a cellular communication network).

Those skilled in the art will appreciate that the environments illustrated in FIGS. 1-6 are not intended to limit embodiments of the present disclosure. For example, it will be appreciated that the control unit 120, interactive pillow 130 and/or portable electronic device 132 may each be under the control of an operating system (not shown) and execute, or otherwise rely upon, various computer software applications, sequences of operations, components, programs, application, files, objects, modules, etc., consistent with embodiments of the invention. In specific embodiments, it will be appreciated that the portable electronic device 132 may be configured to receive various computer software applications, sequences of operations, components, programs, application, files, objects, modules, etc. that may be specific to communicating with the control unit 120 and operating the adjustable bed 10.

Moreover, and in some embodiments, at least one of memory 142, 162 and/or 182 of the respective control unit 120, interactive pillow 130 and/or portable electronic device 132 may include at least one audio file. As such, any of the control unit 120, interactive pillow 130 and/or portable electronic device 132 may play that audio file in an attempt to awaken the person. Specifically, the audio file may include a voice, music, alarm, indication and/or information that may be played in an attempt to awaken the person. Similarly, at least one of memory 142, 162 and/or 182 of the respective control unit 120, interactive pillow 130 and/or portable electronic device 132 may include at least one voice recognition application to convert voiced utterances of a user into machine readable input as well as determine when the person is snoring. Thus, at least one of the control unit 120, interactive pillow 130 and/or portable electronic device 132 may be configured to determine when to adjust and/or awaken a person.

Additionally, it will be appreciated by one having ordinary skill in the art that the control unit 120 may be configured to actuate more or fewer motors 86 and/or vibration units 128. Similarly, it will be appreciated that the control unit 120 may be configured to actuate at least one pump (not shown) in fluid communication with a fluid reservoir (not shown) disposed in the mattress 12 of the bed 10. As such, the firmness of the mattress 12 may be adjusted.

The routines executed to implement the embodiments of the invention, whether implemented as part of an operating system or a specific application, component, program, object, module or sequence of instructions executed at least in part by one or more computing systems will be referred to herein as a "sequence of operations," a "program product," or, more simply, "program code." The program code typically comprises one or more instructions that are resident at various times in various memory and storage devices in a computing system, and that, when read and executed by one or more processors of the computing system, cause that computing system to perform the steps necessary to execute steps, elements, and/or blocks embodying the various aspects of the invention.

While the invention has and hereinafter will be described in the context of fully functioning computing systems, those skilled in the art will appreciate that the various embodiments of the invention are capable of being distributed as a program product in a variety of forms, and that the invention applies equally regardless of the particular type of computer readable signal bearing media used to actually carry out the distribution. Examples of computer readable signal bearing media include but are not limited to physical and tangible recordable type media such as volatile and nonvolatile memory devices, floppy and other removable disks, hard disk drives, optical disks (e.g., CD-ROM's, DVD's, etc.), among others, and transmission type media such as digital and analog communication links.

In addition, various program code described hereinafter may be identified based upon the application or software component within which it is implemented in a specific embodiment of the invention. However, it should be appreciated that any particular program nomenclature that follows is used merely for convenience, and thus the invention should not be limited to use solely in any specific application identified and/or implied by such nomenclature. Furthermore, given the typically endless number of manners in which computer programs may be organized into routines, procedures, methods, modules, objects, and the like, as well as the various manners in which program functionality may be allocated among various software layers that are resident within a typical computer (e.g., operating systems, libraries, APIs, applications, applets, etc.), it should be appreciated that the invention is not limited to the specific organization and allocation of program functionality described herein.

Figure 7:
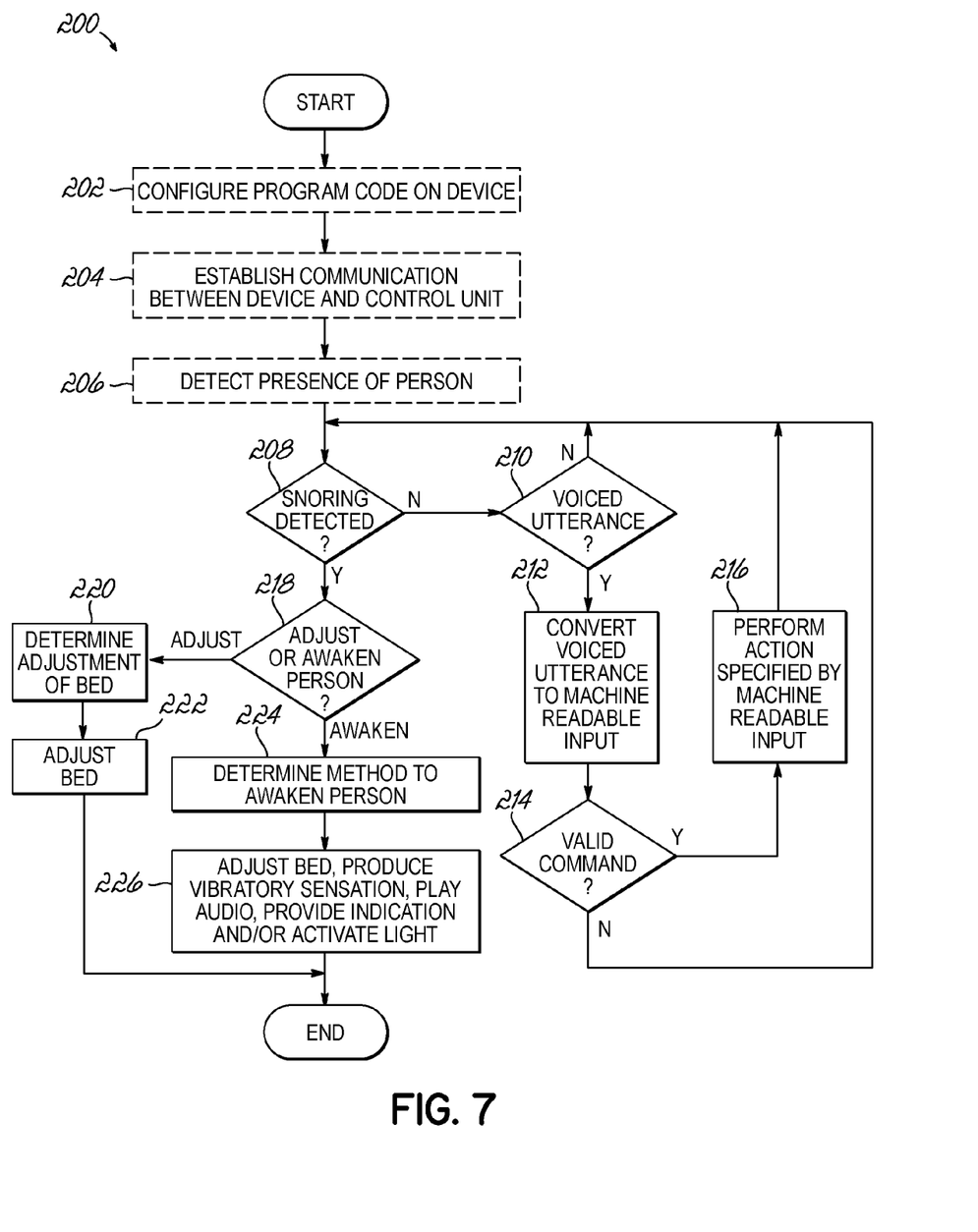
FIG. 7 is a flowchart illustrating a sequence of operations to adjust the adjustable bed of FIG. 1 and/or awaken the person sleeping thereupon.

FIG. 7 is a flowchart illustrating a sequence of operations 200 that may be used to set up the monitoring of a person in an adjustable bed, as well as adjust and/or awaken that person in response to detecting their snoring consistent with embodiments of the invention. In an optional operation, program code may be configured on a device configured to monitor the person (block 202). For example, the program code may be configured on a device (e.g., an interactive pillow and/or a portable electronic device) configured with at least one microphone, speaker, elevation control, movement sensor, vibration unit and/or output device. As such, and in another optional operation, the communication may be established between the device and a control unit configured to control the positions of various portions of the bed (block 204). For example, the interactive pillow and/or portable electronic device may communicate with the control unit through radio frequency communications (e.g., a wireless communications protocol). In another optional operation, the presence of a person on the bed may be detected (block 206). For example, the interactive pillow may include at least one movement sensor, which may in turn be configured to detect the presence of a user interacting with that pillow and/or the bed. As such, prior to attempting to detect snoring of the person it may be a prerequisite that the person actually interact with the interactive pillow (e.g., the person lays on the bed and/or the pillow).

The device and/or the control unit may be configured to detect whether a sound or noise is consistent with snoring of the person (block 208). It may be determined, at the device, whether a noise is snoring or, alternatively, the device may transmit noise it picks up through the microphone to the control unit for the control unit to determine whether a noise is snoring. Specifically, a characteristic of a snore may be stored and compared to a noise picked up by a microphone. As such, when the noise is not a snore (e.g., snoring is not detected) ("No" branch of decision block 208) it may be determined whether a noise is a voiced utterance (e.g., whether the noise is a voice command) (block 210). When the noise is a voiced utterance ("Yes" branch of decision block 210) the voiced utterance is converted into machine readable input (e.g., by the device or by the control unit) (block 212) it is determined whether the machine readable input is a valid command (block 214). When the machine readable input is a valid comment ("Yes" branch of decision block 214) an action specified by the machine readable input is performed (block 216). For example, the voiced utterance may be to "Elevate Head," at which point the voiced utterance may be converted into a command for the control unit to actuate a motor associated with the head of the bed and elevate the head of the bed. Similarly, and also for example, the voiced utterance may be to "Increase Firmness," at which point the voiced utterance may be converted into a command for the control unit to actuate a pump associated with a fluid reservoir disposed in the mattress and increase the firmness of the mattress. When the noise is not a voiced utterance ("No" branch of decision block 210) or when the machine readable input is not a valid command (e.g., for example, the person may be talking in their sleep) ("No" branch of decision block 214) the sequence of operations 200 may return to determining whether snoring of the person is detected (block 208).

When noise is a snore (e.g., snoring is detected) ("Yes" branch of decision block 208) it may be determined whether the bed should be adjusted or the person should be awaken (block 218). For example, if a threshold of snores have been detected, it may be determined that a person should be awakened despite previous bed adjustments. Also for example, if an option has been set to awaken a person instead of adjust the bed, then it may be determined that a person should be awakened. Furthermore for example, if it is not possible to adjust the head and/or foot of the bed any higher it may be determined that a person should be awakened. When it is determined that the bed should be adjusted ("Adjust" branch of decision block 218) the device and/or control unit may determine how to adjust the bed (block 220). Specifically, the current position of the bed may be determined and thus it may be determined whether to raise and/or lower the head and/or foot of the bed. For example, if the bed is in a relatively flat position, it may be determined to slightly raise the head and/or foot of the bed to reduce the snoring of the person. Also for example, if the head and/or foot of the bed is slightly raised, it may be determined to further raise and/or low the head and/or foot of the bed to reduce the snoring of the person. As such, and in response to determining how to adjust the bed, the bed may be adjusted (block 222).

When it is determine that the person should be awakened ("Awaken" branch of decision block 218) the device and/or control unit may determine a method to awaken the person (block 224). Specifically, it may be determined whether to adjust the bed, produce a vibratory sensation, play audio (e.g., including playing an audio file and/or sounding an alarm), provide an indication (e.g., through an output device of the device) and/or activate a light. In response to determining the method to awaken the person, the bed may be adjusted, a vibratory sensation may be produced, audio may be played, an indication may be provided and/or a light may be activated (block 226).

Figure 8:
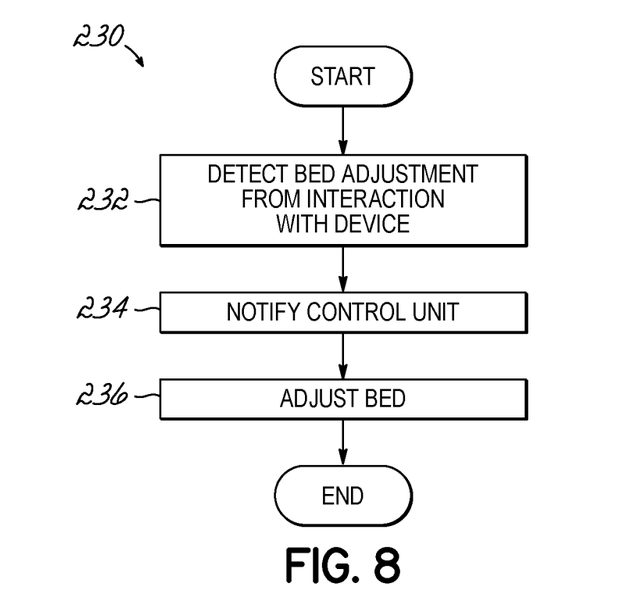
FIG. 8 is a flowchart illustrating a sequence of operations to detect interaction from the interactive pillow and/or portable electronic device of FIG. 1 to adjust the adjustable bed of FIG. 1.

FIG. 8 is a flowchart illustrating a sequence of operations 230 that may be used to adjust at least a portion of a bed consistent with embodiments of the invention. Specifically, interaction with a device to adjust at least a portion of the bed may be detected (block 232). For example, the interaction may be with at least one elevation control of an interactive pillow, an output device of a portable electronic device, and/or a microphone of at least one of the interactive pillow or portable electronic device. As such, the interaction may be determined to be a request to adjust the bed. Thus, the control unit configured to adjust the bed may be notified (block 234) and the bed may be in turn adjusted by the control unit (block 236).

Figure 9:
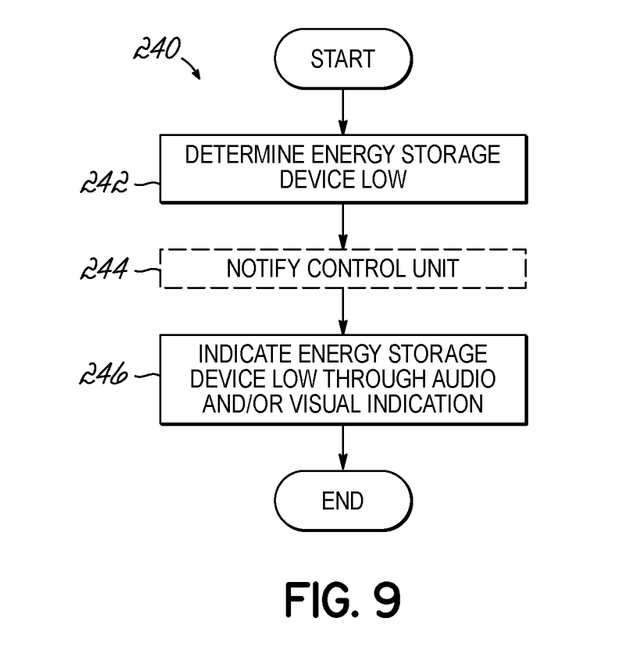
FIG. 9 is a flowchart illustrating a sequence of operations to determine that an energy storage device of the interactive pillow and/or the portable electronic device of FIG. 1 is low and thus provide an indication thereof.

FIG. 9 is a flowchart illustrating a sequence of operations 240 that may be used to indicate the low output state of an energy storage device consistent with embodiments of the invention. In particular, a device may determine that an energy storage device associated therewith is low (e.g., the interactive pillow and/or portable electronic device determines that the power from an energy storage device associated therewith has fallen below a specific threshold) (block 242). As such, and in an optional step, a control unit may be notified (block 244). In response to determining that an energy storage device associated with a device is low and/or in response to determining that a control unit has instructed a device to do so, the low output of the energy storage device may be indicated through an audio and/or visual indication (block 246). Specifically, audio may be played, an indication may be provided and/or a light may be activated.

Figure 10:
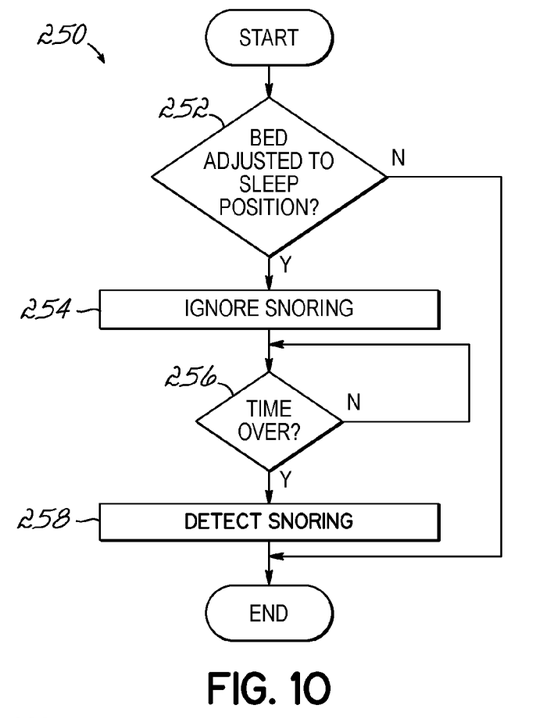
FIG. 10 is a flowchart illustrating a sequence of operations to ignore snoring of a person sleeping on the adjustable bed of FIG. 1.

FIG. 10 is a flowchart illustrating a sequence of operations 250 to ignore snoring of a person consistent with embodiments of the invention. Specifically, the sequence of operations 250 may be used in connection with the sequence of operations 200 illustrated in FIG. 7 to adjust the bed. Returning to FIG. 10, after a bed has been adjusted (e.g., as in blocks 216, 222 and/or 226 of FIG. 7), it may be determined whether a bed has been adjusted to a sleep position (e.g., the bed and/or mattress is in a substantially flat orientation and/or in a position specified by a person as their preferred sleep position) (block 252). When the bed has been adjusted to the sleep position ("Yes" branch of decision block 252), any noise consistent with snoring of the person may be ignored for a period of time (block 254). In this manner, the person may be provided with a chance during which to fall back to sleep before snoring is again detected. Thus, it may be determined whether the period of time is over (block 256). When the period of time is not over ("No" branch of block 256) it may be again determined whether the period of time is over. When the period of time is over ("Yes" branch of block 256) any noise consistent with snoring may again be detected (block 258). In some embodiments the period of time is about thirty minutes. It will be appreciated that, in alternative embodiments, the sequence of operations 250 illustrated in FIG. 10 may be executed after any adjustment to the bed, and thus the present disclosure should not be limited to only ignoring snoring for a period of time after a bed has been adjusted to a sleep position.

Figure 11:
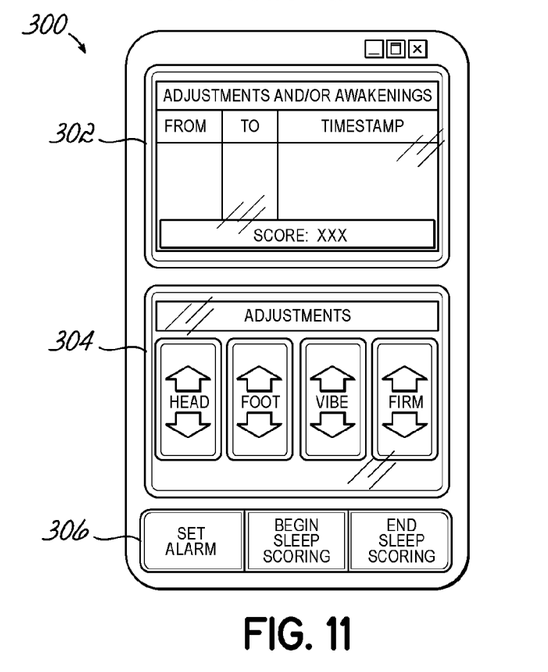
FIG. 11 is a display representation of an information and control screen that may be provided by the portable electronic device of FIG. 1.

Further details and embodiments of the present invention will be described by way of the following examples FIG. 11 is a display representation of an information and bed control screen 300 (hereinafter, "screen" 300) that may be provided by an output device of a portable electronic device consistent with embodiments of the invention. In particular, the screen 300 illustrates an information module 302, an adjustment module 304 and a control module 306. The information module 302 may include information associated with adjustments of the bed, including what position the bed started at as well as the position that the bed ended at. Additionally, the information module may include timestamps of the adjustments. Moreover, the information module 302 may include information about attempted awakenings of the person as well as the amount of time that the person slept. This information (e.g., adjustments as well as their times and frequencies, awakenings as well as their times and frequencies, as well as total time a person slept) may be analyzed to determine a sleep score, or an objective measure of the quality of sleep of the person as illustrated in the information module 302.

The adjustment module 304, on the other hand, may be interacted with by the person to adjust the head and/or foot of the bed, the vibratory sensations produced by at least one vibratory unit and/or the firmness of the mattress associated with the bed. The control module may be interactive with by the person to set an alarm at which to wake, begin sleep scoring and/or end sleep scoring.

While the present invention has been illustrated by a description of the various embodiments and the examples, and while these embodiments have been described in considerable detail, it is not the intention of the applicants to restrict or in any way limit the scope of the appended claims to such detail. For example, although some information and control options are illustrated in FIG. 11, it will be appreciated by one having ordinary skill in the art that additional information, such as reports detailing additional information, may be displayed. Moreover, it will be appreciated by one having ordinary skill in the art that additional control options may be displayed.

Additional advantages and modifications will readily appear to those skilled in the art. Thus, the invention in its broader aspects is therefore not limited to the specific details, representative apparatus and method, and illustrative example shown and described. In particular, any of the blocks of the above flowcharts may be deleted, augmented, made to be simultaneous with another, combined, or be otherwise altered in accordance with the principles of the present invention. For example, although the blocks of FIGS. 7-10 are illustrated as being in a specific order, any of the blocks of FIGS. 7-10 may be combined, made concurrent, and/or re-ordered without departing from the scope of the invention. Accordingly, departures may be made from such details without departing from the spirit or scope of applicants' general inventive concept

What is claimed is:

1. A system to reduce snoring of a person sleeping on an adjustable bed, the system comprising:
    a device including at least a processing unit, a memory and a network interface and an output device, the device being configured with at least a microphone and a speaker, the device configured to monitor for a noise consistent with snoring wherein the device is configured to provide a display representation that indicates information about previous adjustments of the adjustable bed; and a control unit communicably coupled to the device and configured to actuate at least one motor of the adjustable bed to adjust at least a portion of the adjustable bed, wherein the control unit is further configured to actuate the at least one motor in response to the device detecting a noise consistent with snoring.

2. The system of claim 1, wherein the device includes at least one elevation control to adjust the at least a portion of the adjustable bed, and wherein the pillow is configured to determine interaction with the at least one elevation control to adjust that at least a portion of the adjustable bed.

3. The system of claim 1 wherein the device is configured to play an audio signal on the speaker in response to the device detecting snoring of the person.

4. The system of claim 1, wherein the device includes a pillow portion.

5. The system of claim 1, wherein the device is configured to determine if power from an energy storage device associated therewith is low and, in response to such determination, provide an indication to the person.

6. The system of claim 1, wherein the device is configured to convert a voiced utterance of the person into machine readable input to adjust the at least a portion of the adjustable bed.

7. The system of claim 1, wherein the device is configured to communicate wirelessly with the control unit.

8. A system to reduce snoring of a person sleeping on an adjustable bed, the system comprising:
a device including at least a processing unit, a memory and a network interface and an out ut device the device bein confi ured with at least a micro hone and a s eaker the device configured to monitor for a noise consistent with snoring; and
a control unit communicably coupled to the device and configured to actuate at least one motor of the adjustable bed to adjust at least a portion of the adjustable bed, wherein the control unit is further configured to actuate the at least one motor in response to the device detecting a noise consistent with snoring, wherein the device is configured to provide a display representation that indicates a quality of sleep of the person.

9. The system of claim 8, wherein the device is configured to provide a display representation that is interactable to adjust at least a portion of the adjustable bed.

10. A system to reduce snoring of a person sleeping on an adjustable bed, the system comprising:
a device configured with at least a microphone and a speaker, the device configured to monitor for a noise consistent with snoring; and
a control unit communicably coupled to the device and configured to actuate at least one motor of the adjustable bed to adjust at least a portion of the adjustable bed, wherein the control unit is further configured to actuate the at least one motor in response to the device detecting a noise consistent with snoring, wherein the device is configured to detect the presence of a person prior to detecting snoring of the person.

11. A system to reduce snoring of a person sleeping on an adjustable bed, the system comprising:
a device configured with at least a microphone and a speaker, the device configured to monitor for a noise consistent with snoring; and
a control unit communicably coupled to the device and configured to actuate at least one motor of the adjustable bed to adjust at least a portion of the adjustable bed, wherein the control unit is further configured to actuate the at least one motor in response to the device detecting a noise consistent with snoring, wherein the device is configured to ignore snoring of the person for a period of time in response to determining that the adjustable bed has been adjusted to a sleep position.

12. A method to reduce snoring of a person sleeping on an adjustable bed, comprising:
monitoring for a noise consistent with snoring with a device; and
in response to detecting a noise consistent with snoring, actuating at least one motor of a control unit. and providing a display representation regarding previous adjustments of the adjustable bed.

13. The method of claim 12, further comprising:
determining interaction with the device to adjust the at least a portion of the adjustable bed.

14. The method of claim 12, further comprising:
in response to detecting the noise consistent with snoring, playing an audio signal.

15. A method to reduce snoring of a person sleeping on an adjustable bed, the method comprising:
monitoring for a noise consistent with snoring with a device;
in response to detecting a noise consistent with snoring, actuating at least one motor of a control unit; and
providing information about previous adjustments of the adjustable bed with the device.

16. A method to reduce snoring of a person sleeping on an adjustable bed the method comprising:
monitoring for a noise consistent with snoring with a device;
in response to detecting a noise consistent with snoring, actuating at least one motor of a control unit; and
providing an indication of a quality of sleep of the person.

17. The method of claim 16, wherein providing the indication further comprises:
analyzing previous adjustments of the adjustable bed; and
analyzing movement of the person during their sleep.

18. The method of claim 16, further comprising:
adjusting a vibratory sensation associated with the at least a portion of the adjustable bed.

19. The method of claim 16, further comprising:
adjusting a firmness associated with the at least a portion of the adjustable bed.

20. A method to reduce snoring of a person sleeping on an adjustable bed, the method comprising:
monitoring for a noise consistent with snoring with a device;
in response to detecting a noise consistent with snoring, actuating at least one motor of a control unit; and
detecting the presence of the person with the device.

21. The method of claim 20, further comprising:
in response to determining that power provided by an energy storage device associated with the device is low, providing an indication of that low power to the person.

22. The method of claim 20, further comprising:
converting a voiced utterance of the person into machine readable input to adjust the at least a portion of the adjustable bed.

23. A method to reduce snoring of a person sleeping on an adjustable bed, the method comprising:
monitoring for a noise consistent with snoring with a device;
in response to detecting a noise consistent with snoring, actuating at least one motor of a control unit; and
in response to determining that the adjustable bed has been adjusted to a sleep position, ignoring a noise consistent with snoring for a period of time.

24. A method to adjust an adjustable bed, the method comprising:
- monitoring a sleeping person for a noise consistent with snoring with a device;
- in response to detecting a noise consistent with snoring, determining whether to adjust the adjustable bed or attempt to awaken the person;
- in response to determining to adjust the adjustable bed, actuating at least one motor of the adjustable bed with a control unit and detecting the presence of the person with the device.

25. The method of claim 24, further comprising:
- in response to determining to attempt to awaken the person, actuating at least one motor of the adjustable bed with the control unit.

26. The method of claim 24, further comprising:
- in response to determining to attempt to awaken the person, producing a vibratory sensation on at least a portion of the adjustable bed.

27. The method of claim 24, further comprising:
- in response to determining to attempt to awaken the person, playing an audio signal.

28. The method of claim 24, further comprising:
- in response to determining to attempt to awaken the person, providing an indication.

29. The method of claim 24, further comprising:
- in response to determining to attempt to awaken the person, activating a light.

* * * * *

UNITED STATES PATENT AND TRADEMARK OFFICE
CERTIFICATE OF CORRECTION

PATENT NO. : 8,410,942 B2
APPLICATION NO. : 12/787091
DATED : April 2, 2013
INVENTOR(S) : Ryan Chacon et al.

It is certified that error appears in the above-identified patent and that said Letters Patent is hereby corrected as shown below:

In the Specification

Column 1

Line 15, "effect" should be --affect--.

Line 42, "conductive" should be --conducive--.

Column 2

Line 14, "FIG. 1 is perspective" should be --FIG. 1 is a perspective--.

Column 4

Line 38, "maybe" should be --may be--.

Column 6

Line 7, "may communicably" should be --may be communicably--.

Column 10

Line 43, "awaken" should be --awakened--.

Line 44, "have been" should be --has been--.

Signed and Sealed this
Twenty-third Day of July, 2013

Teresa Stanek Rea
*Acting Director of the United States Patent and Trademark Office*

CERTIFICATE OF CORRECTION (continued)
U.S. Pat. No. 8,410,942 B2

Column 12

Line 26, delete the word "by".

In the Claims

Column 13

Claim 8, Lines 30-31, "a network interface and an out ut device the device beinconiured with at least a micro hone and a s eaker the" should be --a network interface and an output device, the device being configured with at least a microphone and a speaker, the--.

Column 14

Claim 12, Line 10, after "control unit", should be a new paragraph.

Claim 16, Line 28, after "adjustable bed", insert a --,--.